(12) United States Patent
Skriner

(10) Patent No.: US 9,221,881 B2
(45) Date of Patent: Dec. 29, 2015

(54) MARKERS FOR THE DIAGNOSIS OF CELIAC DISEASE

(75) Inventor: Karl Skriner, Berlin (DE)

(73) Assignee: Charité-Universitätsmedizin Berlin, Berlin (DE)

( * ) Notice: Subject to any disclaimer, the term of this patent is extended or adjusted under 35 U.S.C. 154(b) by 944 days.

(21) Appl. No.: 13/499,678

(22) PCT Filed: Oct. 1, 2010

(86) PCT No.: PCT/EP2010/064650
§ 371 (c)(1),
(2), (4) Date: Mar. 30, 2012

(87) PCT Pub. No.: WO2011/039350
PCT Pub. Date: Apr. 7, 2011

(65) Prior Publication Data
US 2012/0225442 A1    Sep. 6, 2012

(30) Foreign Application Priority Data

Oct. 1, 2009 (DE) .......................... 10 2009 045 268

(51) Int. Cl.
  *C07K 14/00* (2006.01)
  *G01N 33/564* (2006.01)
  *G01N 33/68* (2006.01)
  *G01N 33/58* (2006.01)
  *G01N 33/543* (2006.01)

(52) U.S. Cl.
  CPC .............. *C07K 14/00* (2013.01); *G01N 33/543* (2013.01); *G01N 33/564* (2013.01); *G01N 33/581* (2013.01); *G01N 33/68* (2013.01); *G01N 33/6854* (2013.01)

(58) Field of Classification Search
  None
  See application file for complete search history.

(56) References Cited

U.S. PATENT DOCUMENTS

| 7,462,688 | B2 * | 12/2008 | Khosla et al. ................. 530/326 |
| 7,776,545 | B2 * | 8/2010 | Khosla et al. ................. 435/7.1 |
| 2005/0249719 | A1 | 11/2005 | Shan et al. |
| 2014/0302045 | A1 * | 10/2014 | Skriner ...................... 424/139.1 |

FOREIGN PATENT DOCUMENTS

WO    WO2005/105129    11/2005

OTHER PUBLICATIONS

Villalta et al., Testing for IgG class antibodies in celiac disease patients with selective IgA deficiency, *Clinica Chimica ACTA*, vol. 382, No. 1-2, May 24, 2007 XP022095244.
Lewis N R et al., Meta-analysis: deamidatd gliadin peptide antibody and tissue transglutaminase antibody compared as screening tests for coeliac disease, *Alimentary Pharmacology & Therapeutics*, vol. 31, No. 1 Jan. 1, 2009, XP002610336.
Martini, S et al., Diagnostic Accuracies for Celiac Disease of Four Tissue Transglutaminase Autoantibody Tests Using Human Antigen, *Clinical Chemistry* 47, No. 9 (2001).
International Search Report dated Nov. 22, 2010 Application No. PCT/EP2010/064650 (3 pages total).

* cited by examiner

*Primary Examiner* — Christine Foster
(74) *Attorney, Agent, or Firm* — VLP Law Group LLP; Kent H. Cheng

(57) ABSTRACT

The invention relates to new peptides and to their use in the diagnosis of celiac disease.

13 Claims, 4 Drawing Sheets

| negative characteristics | Number of negative sera | positive sera by assay [%] | | | | |
|---|---|---|---|---|---|---|
| | | tTG IgA | tTG IgG | Gliadin IgA | Gliadin IgG | CDP Peptid |
| tTG IgA negativ | 26 | (n.e.4) | 46 | 15 | 46 | 46 |
| tTG IgG negativ | 31 | 55 | (n.e.4) | 39 | 29 | 52 |
| Gliadin IgA negativ | 38 | 42 | 50 | (n.e.4) | 42 | 55 |
| Gliadin IgG negativ | 41 | 66 | 49 | 46 | (n.e.4) | 71 |
| CDP negativ | 20 | 30 | 25 | 20 | 40 | (n.e.4) |
| tTG IgA/ IgG negativ | 14 | (n.e.4) | (n.e.4) | 21 | 36 | 29 |
| Gliadin IgA/IgG negativ | 22 | 55 | 41 | (n.e.4) | (n.e.4) | 64 |
| tTG IgA; Gliadin IgA negativ | 22 | (n.e.4) | 50 | (n.e.4) | 55 | 46 |
| tTG IgA; Gliadin IgG negativ | 14 | (n.e.4) | 50 | 29 | (n.e.4) | 50 |
| tTG IgG; Gliadin IgA negativ | 19 | 42 | (n.e.4) | (n.e.4) | 32 | 37 |
| tTG IgG; Gliadin IgG negativ | 22 | 59 | (n.e.4) | 45 | (n.e.4) | 50 |
| tTG IgA/IgG; Gliadin IgA negativ | 11 | (n.e.4) | (n.e.4) | (n.e.4) | 45 | 27 |
| tTG IgA/IgG; Gliadin IgG negativ | 9 | (n.e.4) | (n.e.4) | 33 | (n.e.4) | 33 |
| Gliadin IgA/IgG; tTG IgA negativ | 10 | (n.e.4) | 40 | (n.e.4) | (n.e.4) | 50 |
| Gliadin IgA/IgG; tTG IgG negativ | 12 | 50 | (n.e.4) | (n.e.4) | (n.e.4) | 42 |
| tTG; Gliadin negativ | 6 | (n.e.4) | (n.e.4) | (n.e.4) | (n.e.4) | 30 |

Fig. 3

MARKERS FOR THE DIAGNOSIS OF CELIAC DISEASE

PRIORITY CLAIM

This is a U.S. national stage of application No. PCT/EP10/064650, filed on Oct. 1, 2010.Priority is claimed on the following applications: German Application NO.: 10 2009 045 268.0 Filed on Oct. 1, 2009, the contents of which are incorporated here by reference.

SEQUENCE LISTING

The instant application contains a Sequence Listing which has been submitted in ASCII format via EFS-Web and is herby incorporated by reference in its entirety. Said ASCII copy, created on Apr. 26, 2012, is named 566129PU.txt and is 20,834 bytes in size.

BACKGROUND OF THE INVENTION

Celiac disease (according to ICD-10, WHO 2006 version: K90.0), also referred to as gluten-sensitive or gluten-induced enteropathy, intestinal infantilism; or non-tropical or endemic sprue, gluten intolerance or Heubner-Herter disease in adults, is a chronic disease of the small intestinal mucosa resulting from a hypersensitivity to gluten, a protein which is found in many types of grains. The intolerance remains throughout life and is in part genetically determined and cannot at present be treated causally.

Foods containing gluten give rise to inflammation of the small intestinal mucosa with frequently extensive destruction of the intestinal epithelial cells, so that nutrients are poorly absorbed and remain undigested in the bowels. Accordingly, the symptoms are weight loss, diarrhea, vomiting, anorexia, fatigue, ill-humor and, not least, failure to thrive during infancy. The severity of the condition can vary widely, making early diagnosis more difficult. Untreated celiac disease increases the risk of occurrence of non-Hodgkin lymphoma as well as carcinomas of the digestive tract, such as intestinal cancer. At present, the only treatment of celiac disease consists in gluten-free diet.

Meanwhile, a number of harmful peptide fragments of gluten have been identified. They all belong to the alcohol-soluble fraction (so-called prolamins) and are referred to as gliadin. In susceptible individuals, these peptide fragments give rise to a complex reaction of the intestinal mucosa and immune system. Mucosal cells of the small intestine produce increasing amounts of various classes of HLA (HLA-I, -DR and -DQ). Certain gliadin peptides bind to the HLA-DQ2 produced in increasing amounts. Said binding is increased as a result of glutamic acid formation from the amino acid glutamine which is present in the peptide in large numbers.

Formation of glutamic acid is mediated by the tissue transglutaminase enzyme, in particular tissue transglutaminase 2 (tTG2). As a result of this change, the corresponding section of gliadin has a better fit in the "pockets" of HLA proteins. The complex of gliadin peptide and HLA-DQ2 in turn binds to CD4+ T helper cells, causing increased production of various inflammatory mediators therein, for instance interferon-γ, TNFα, interleukin-6 and interleukin-2. Various antibodies are formed during the further process of inflammation. In addition to antibodies against gliadin peptides themselves (gliadin antibodies, AGA), there are so-called autoantibodies against endogenous antigens. Tissue transglutaminase, particularly tTG2, has been identified as primarily responsible autoantigen. In view of these findings, celiac disease in pathophysiological terms is understood to be a mixed form of allergy and autoimmune disease, wherein the allergic component in the form of hypersensitivity to the exogenous gliadin protein represents the precipitating factor, while the autoimmune response to endogenous structures is responsible for the severity of symptoms. Ultimately, the inflammatory process results in apoptosis of enterocytes, eventually leading to a more or less pronounced loss of small intestinal villi. As a result of the reduced absorption surface, the small intestinal mucosa damaged in this way is no longer capable of sufficiently transferring the supplied foods into the bloodstream.

In general, serological diagnostics of celiac disease involves testing for the presence of IgA and/or IgG type antibodies to gliadin or tTG2. One problem of well-known diagnostic markers is that the sensitivity of the tests is not yet optimal. Particularly the tests for the presence of gliadin antibodies exhibit low sensitivities of less than 80%. While well-known tests for tTG2 antibodies are more sensitive on the whole, the informative epitopes of tTG2 are so-called conformational epitopes, i.e. epitopes that can be recognized by antibodies only if tTG2 is presented in a non-denatured state. Consequently, tests for tTG2 antibodies are limited to those test methods wherein the tTG2 antigen is presented in a non-denatured state.

SUMMARY OF THE INVENTION

The object of the present invention is to alleviate or avoid one or more draw-backs of the prior art. More specifically, the object of the present invention is to provide new markers for the diagnosis of celiac disease.

Said object is accomplished by providing a peptide containing or consisting of an amino acid sequence of SEQ ID NO: 1. In a preferred fashion the peptide according to the invention may contain or consist of an amino acid sequence of SEQ ID NO: 2, SEQ ID NO: 3, or SEQ ID NO: 4.

The present invention is based on the surprising finding that the peptide according to the invention is specifically recognized by antibodies produced in celiac patients. It was shown that the peptide of the invention can be used to identify even those celiac patients wherein recognition by means of one or more conventional serological celiac diagnostic tests has not been possible. Moreover, it was demonstrated that the peptide according to the invention is not a so-called conformational epitope but can also be recognized in denatured form by antibodies from patient sera. Consequently, the peptide is also suitable for types and variants of tests in which e.g. tTG2-based assays cannot be used as yet and wherein the epitope for antibody detection is used in denatured state, such as Western blot procedures. More specifically, it was shown that a peptide according to the invention, comprising a sequence of SEQ ID NOs: 1, 2, 3 and 4, and the sequence of human tTG2 can be used to provide a diagnostic assay for celiac disease which has a sensitivity that is higher than the sensitivity of any known diagnostic assay for celiac disease.

For the purpose of the present invention, the term "peptide" is understood to denote any molecule having a peptide bond between at least two amino acids. A peptide bond (—NH—CO—) is an amide-type bond between the carboxyl group of a first amino acid and the amino group of a second amino acid. In principle, the term "peptide" therefore comprises dipeptides, oligopeptides, polypeptides and proteins, which peptides may have modifications.

The peptide according to the invention has at least one amino acid sequence of SEQ ID NO: 1 and thus at least one amino acid sequence having 24 amino acids. Moreover, the peptide of the invention may comprise additional amino acids or amino acid sequences.

Amino acids are a class of organic compounds with at least one carboxyl group (—COOH) and one amino group (—NH$_2$). The amino acids present in the peptide according to the invention are preferably α-, β- or γ-amino acids, more preferably α-amino acids. Amino acids of the 20 naturally occurring amino acids, but also non-naturally occurring α-, β- or γ-amino acids, can be included in the peptide.

One or more amino acids of the peptide according to the invention can be modified. A modified amino acid is understood to be an amino acid which bears a functional group on its side chain. The characteristic feature of a functional group is that the group imparts an additional function or property to the peptide, which is not or not sufficiently present in the peptide of the invention without the functional group, said functional group not being directly involved in specific binding of the peptide of the invention to antibodies from sera of celiac patients. Examples of functional groups are marker groups, such as GFP, His tag, AVI tag, biotin tag, etc., allowing, for example, detection, accumulation and/or purification of the peptide according to the invention. Other functional groups are coupling groups allowing e.g. reversible or irreversible coupling or immobilization of the inventive peptide to other molecules and/or carriers. With the aid of such coupling groups the peptide according to the invention can be, for example, bound to a molecule, such as BSA, or a microparticle, or can be immobilized on a carrier suitably prepared, if necessary. For example, a biotinylated peptide can be immobilized very effectively on a surface pre-treated with streptavidin (neutravidin). Examples of such coupling groups are biotin, streptavidin, etc., but it is also possible to use chemically reactive groups such as carboxyl, amino or amide groups. Suitable marker and/or coupling groups are well-known to those skilled in the art.

Apart from optional modifications present on the side chains of individual amino acids of the peptide according to the invention, the present invention also comprises peptides bearing modifications on their N- and/or C-terminal ends. In addition to the above-mentioned functional groups, the peptide may have functional groups on the N- and/or C-terminal ends which e.g. increase the stability of the peptide or facilitate the accessibility of the epitope included in the peptide according to the invention. Thus, for example, the peptide can be made more stable by coupling the peptide to antibodies.

The peptide according to the invention may have further amino acid sequences in addition to the amino acid sequences of SEQ ID NOs: 1, 2, 3 and/or 4. For example, the peptide may comprise a plurality of copies of a single sequence of SEQ ID NOs: 1, 2, 3 and 4.

The peptide according to the invention may have one or more amino acid sequences acting as linkers and/or functional groups. Thus, for example, two amino acid sequence regions of a peptide can be bound to each other by a linker. For example, an amino acid sequence which connects via peptide bonds two parts of the inventive peptide to be bound, so as to form a continuous amino acid chain, can be referred to as linker. Such linkers can also be referred to as peptide linkers. A part of the peptide according to the invention may also be in the form of a functional group. Such a functional group may involve the functional groups described above, attached on a side chain of one or more amino acids of the peptide according to the invention or situated at the N- and/or C-terminal ends of the peptide. Also, they can be in the form of an amino acid sequence and represent an integral component of the continuous amino acid chain of the peptide according to the invention. Such peptidic functional groups may comprise amino acid chains having one or more amino acids or may comprise entire proteins or functional subunits of proteins. Examples of such functional groups are markers used in detection and purification, such as His tag, GFP, etc., or selected epitopes, such as portions or the entire sequence of human tTG2 (human tissue transglutaminase 2) of SEQ ID NO: 5.

More specifically, the peptide according to the invention may additionally comprise a sequence of at least 25 consecutive amino acids, preferably 100 consecutive amino acids, from the sequence of human tTG2 of SEQ ID NO: 5. In principle, the portions forming part of the peptide according to the invention can be selected from any part of the tTG2 sequence of SEQ ID NO: 5. In a preferred fashion the portion is selected such that it comprises at least one epitope that can be recognized by antibodies from sera of celiac patients. In a particularly preferred fashion the peptide of the invention comprises one or more partial sequences of tTG2 or one or more copies of the entire sequence of tTG2 of SEQ ID NO: 5 in addition to one or more amino acid sequences of SEQ ID NOs: 1, 2, 3 and/or 4. Moreover, the peptide of the invention may comprise additional amino acid sequences and/or functional groups. such as His tag, in particular a 6×His tag(SEQ ID NO: 8). More specifically, the peptide of the invention may have or consist of a sequence of SEQ ID NO: 6 [SEQ ID NOs: 5+2]or SEQ ID NO: 7 [SEQ ID NOs: 5+2+2].

The present invention also relates to an inventive peptide for use as medicament, e.g. for use in diagnosis, especially in the diagnosis of celiac disease.

The peptide according to the invention can be prepared synthetically by controlled linking of selected amino acids. Alternatively, the peptide of the invention can be prepared by genetic engineering wherein a nucleic acid encoding the respective peptide is provided and placed in a context that allows expression and optionally subsequent purification of the encoded peptide. For example, expression can be effected in vitro or in transiently or stably transfected cells or in transformed microorganisms. Suitable methods are well-known to those skilled in the art and have been described e.g. in Molecular Cloning—A Laboratory Manual, 3$^{rd}$ Edition, Cold Spring Harbor Laboratory Press, 2001, or Current Protocols in Molecular Biology, John Wiley and Sons, NY (1989), and following issues.

The present invention also relates to a nucleic acid comprising a nucleic acid sequence encoding a peptide of the invention. A person skilled in the art will be aware that the genetic code is degenerate and, starting from a particular amino acid sequence of the peptide according to the invention, will be able to determine the possible nucleic acid sequences of an inventive nucleic acid without undue effort. Similarly, starting from a given nucleic acid sequence and taking into account the degeneration of the genetic code, a person skilled in the art can clearly and unambiguously determine without undue effort whether or not said given nucleic acid will encode a peptide according to the invention. The nucleic acid of the invention comprises DNA, RNA, mixtures and/or functional derivatives thereof, in particular cDNA, genomic DNA, linear or circular DNA, e.g. vectors, mRNA, linear or circular RNA, and can be prepared partially or completely by way of synthesis or genetic engineering. The nucleic acid can be in single-stranded form or partially or completely in the form of a double strand.

The nucleic acid according to the invention is preferably an isolated nucleic acid. For the purposes of the present invention, "isolated" means that the isolated component has been separated from its natural context. Using the example of an isolated nucleic acid, an exemplary illustration of what the term "isolated" comprises at minimum will be given below. For example, a nucleic acid is isolated if it has been purposefully modified by man and/or if the nucleic acid has been transferred to an environment other than the natural environment or to a place other than the natural locus. Similarly, a nucleic acid is isolated in the meaning of the invention if it exists in a purified form or separated from its natural environment, preferably in a substantially pure and/or homogeneous form, or substantially free of nucleic acids which are not nucleic acids according to the invention. A cloned nucleic acid is generally an isolated nucleic acid.

The present invention also comprises transformed microorganisms or transformed cells comprising a nucleic acid according to the invention. This includes microorganisms and cells either transiently or stably transformed or transfected with a nucleic acid of the invention situated therein, in which event the nucleic acid of the invention may exist e.g. in free form in the microorganism or cell or incorporated in the genome. The microorganisms according to the invention are unicellular organisms, preferably bacteria or unicellular fungi such as yeasts. The cells according to the invention are cells of multicellular organisms, preferably isolated cells, e.g. cells allowing in vitro culturing in a cell culture. For example, the cells can be either primary cells or immortalized cells. In particular, those microorganisms or cells are preferred which can be used or have been used in the preparation of peptides and/or proteins.

The present invention also relates to isolated antibodies that bind to a peptide according to the invention. An antibody is understood to be a protein having one or more specific antigen binding sites (CDR, complementarity determining region). Antibodies in the meaning of the invention include both polyclonal or monoclonal antibodies having a classical antibody structure and derivatives or fragments derived therefrom, such as Fab, $Fab_2$, single chains, etc. Starting from a particular peptide according to the invention, a person skilled in the art is able, without undue effort, to generate an isolated antibody that specifically binds to said peptide. Such techniques and approaches are well-known to those skilled in the art and routine in daily laboratory practice. For example, the isolated antibodies of the invention can also be generated in such a way that, by using a peptide according to the invention, the antibodies present in the serum of celiac patients are isolated, purified and thus made accessible. To this end, the peptide of the invention can be coupled to a support, for example, and the support loaded with peptide is subsequently contacted with celiac patient serum. Non-specifically bound components of the serum are removed, and the antibodies specifically bound to the peptide of the invention are subsequently eluted.

The antibodies according to the invention can be used, for example, for the detection of pathogens, e.g. peptidic pathogens, associated with celiac disease, preferably for the in vitro detection of such pathogens. In a preferred fashion such pathogens can be detected in foods in order to e.g. approve certain foods for celiac patients or delete them from a list of tolerable foods.

The invention also relates to a method for determining the safety of foods intended for consumption by celiac patients, which method is characterized in that the presence of celiac disease-associated pathogens in such foods is determined using the isolated antibodies according to the invention.

The present invention also relates to a method for the in vitro detection of antibodies against a peptide according to the invention in a sample. The method of the invention is characterized in that:

i) a peptide according to the invention is contacted with a sample in vitro, and
ii) antibody bound to the peptide is detected.

For the purposes of the present invention, the term "in vitro" is understood to denote any environment which is not inside a whole organism, e.g. a human or animal body.

An antibody is understood to be a protein having one or more specific antigen binding sites (CDR, complementarity determining region). Antibodies in the meaning of the invention include both polyclonal or monoclonal antibodies having a classical antibody structure and derivatives or fragments derived therefrom, such as Fab, $Fab_2$, single chains, etc.

A sample is understood to be any composition to be investigated. The sample is preferably a biological or medical material, i.e., material obtained from an organism, parts of an organism, or from cells. Prior to use as sample in the method according to the invention, the material can be subjected to further treatment steps in order to e.g. condition the material so as to make it particularly suitable as sample in the method. More preferably, the sample is a material obtained from a body fluid or constituted of a body fluid. Preferred body fluids are blood, plasma, serum, synovial fluid, urine, stool, interstitial fluid, lymph, saliva, sweat, spinal fluid and/or lacrimal fluid. Particularly preferred are those body fluids wherein antibodies are present at high concentrations. Especially preferably, the body fluid is of human origin.

In the method according to the invention, a peptide of the invention is contacted in vitro with a sample to be investigated. The step of contacting is used to enable antibodies possibly included in the sample to bind to an epitope of the peptide according to the invention. To this end, the above step is carried out under conditions and in an environment allowing specific antigen-antibody binding. Suitable conditions are well-known to those skilled in the art. Such conditions preferably comprise a fluid environment and/or contacting at a temperature of from $>0°$ C. to $<60°$ C. Said contacting is preferably carried out for a period of time allowing formation of a specific antigen-antibody bond between the peptide of the invention and a peptide-specific antibody possibly included in the sample. The step of contacting is preferably performed for a period of more than 30 seconds, more preferably more than two minutes, and especially preferably for a period of from two minutes to 48 hours.

Antibody specifically bound to the peptide of the invention is detected in a sub-sequent step of the method according to the invention. For example, antibody specifically bound to the peptide of the invention can be detected in such a way that contacting is followed by removal of sample components not bound to the peptide of the invention, e.g. by means of one or more wash, purification or isolation steps, and subsequent use of agents allowing specific detection of antibodies. The above detection can be effected in one or more steps. For example, the agents used for the specific detection of antibodies can themselves be antibodies. Detection can be effected using e.g. a color reaction mediated or induced directly or indirectly by the agents for the detection of antibodies. For example, the antibodies for the detection of specific antibodies can be bound to functional groups or molecules (e.g. enzymes) capable of mediating or inducing a color reaction under specific conditions.

In the method according to the invention, the peptide of the invention can be immobilized on a support during one or more or all steps of the procedure. Immobilization is understood to be any coupling, binding or other association between the peptide of the invention and the support that prevents separate movement of peptide and support. For example, molecules and/or surfaces configured so as to allow reversible or irreversible binding of the peptide of the invention can be used as support. To this end, the support and/or the peptide of the invention may have functional groups which promote and/or permit binding between peptide and support. Molecules such as BSA, tTG, or surfaces such as presented by microparticles, nanoparticles or magnetic beads, or surfaces of selected membranes, polymers (e.g. polystyrene), or microtiter plates or test strips comprising such surfaces may be mentioned as exemplary supports. Suitable supports and possible ways of binding peptide and support are well-known to those skilled in the art.

More specifically, the method according to the invention can be performed in the form of an immunoassay procedure, and suitable immunoassay procedures have been described in David Wild (Ed.), The Immunoassay Handbook. $3^{rd}$ Edition. Elsevier Science Publishing Company, Amsterdam, Boston, Oxford 2005.

In a preferred fashion the method according to the invention can be performed in the form of an ELISA procedure (ELISA: enzyme-linked immunosorbent assay), and suitable ELISA techniques have been described e.g. in Goldsby, R. A., Kindt, T. J., Osborne, B. A. & Kuby, J. Enzyme-Linked Immunosorbent Assay; in: Immunology, $5^{th}$ ed., pp. 148-150. W. H. Freeman, New York, 2003. To this end, a sample can be contacted with a peptide of the invention immobilized on a support, unbound components are partially or substantially removed, if necessary, and an antibody coupled or couplable to a functional group is subsequently used to detect a sample antibody bound to the peptide. As a rule, detection proceeds via a visually detectable reaction. For example, the antibody used in detection can be specific for antibodies of a particular organism or a particular origin and/or for a specific form of antibody, preferably for a particular isotype, e.g. IgA, IgM and/or IgG type antibodies, more preferably for human IgA, IgM and/or human IgG.

The method according to the invention can also be carried out in other assay formats, preferably e.g. as an RIA (radio-immunological assay) or as an immunoassay in a test strip format.

The present method is suitable for the detection of antibodies against a peptide according to the invention, particularly for the detection of IgA, IgM and/or IgG type antibodies, preferably for the detection of antibodies of human origin. The method according to the invention can be used in diagnosis, especially in serological diagnosis, preferably in the diagnosis of celiac disease.

The present invention also comprises a kit for carrying out the method according to the invention. To this end, the kit may include a peptide of the invention immobilized on a support. In addition, the kit may include instructions for using the kit and/or performing the inventive method by means of said kit. In a preferred fashion the kit is designed in the form of an ELISA, or in particular as a strip test. That is, the kit according to the invention comprises the peptide of the invention and optionally further components for carrying out the inventive method in a form suitable for performing the method according to the invention in an ELISA and/or strip test format. More specifically, the kit may comprise the inventive peptide coupled to a test strip. The kit according to the invention may optionally include additional components for carrying out the method of the invention. For example, such components may comprise reaction vessels, filters, solutions and/or other agents. In particular, the kit according to the invention may include agents for the detection of antibodies, preferably IgA, IgM and/or IgG type antibodies, more preferably for the detection of antibodies of human origin.

The kit according to the invention can be used for carrying out a method of the invention. More specifically, the kit according to the invention is suitable for use in diagnosis, preferably in serological diagnosis, and especially preferably in the diagnosis of celiac disease.

The kit according to the invention can be characterized in that the kit additionally includes agents for the detection of IgA, IgM and/or IgG type antibodies, preferably for the detection of human IgA, IgM and/or IgG type antibodies.

In particular, the kit according to the invention can be used in the diagnosis of celiac disease.

BRIEF DESCRIPTION OF THE DRAWINGS

Figures:

FIG. 3 shows sensitivity overlaps between the individual forms of ELISA used and indicates the percentage of celiac sera not recognized by the quoted tests that were tested positive with the respective assay.

DETAILED DESCRIPTION OF THE PRESENTLY PREFERRED EMBODIMENTS

EXAMPLES

Figure 1:
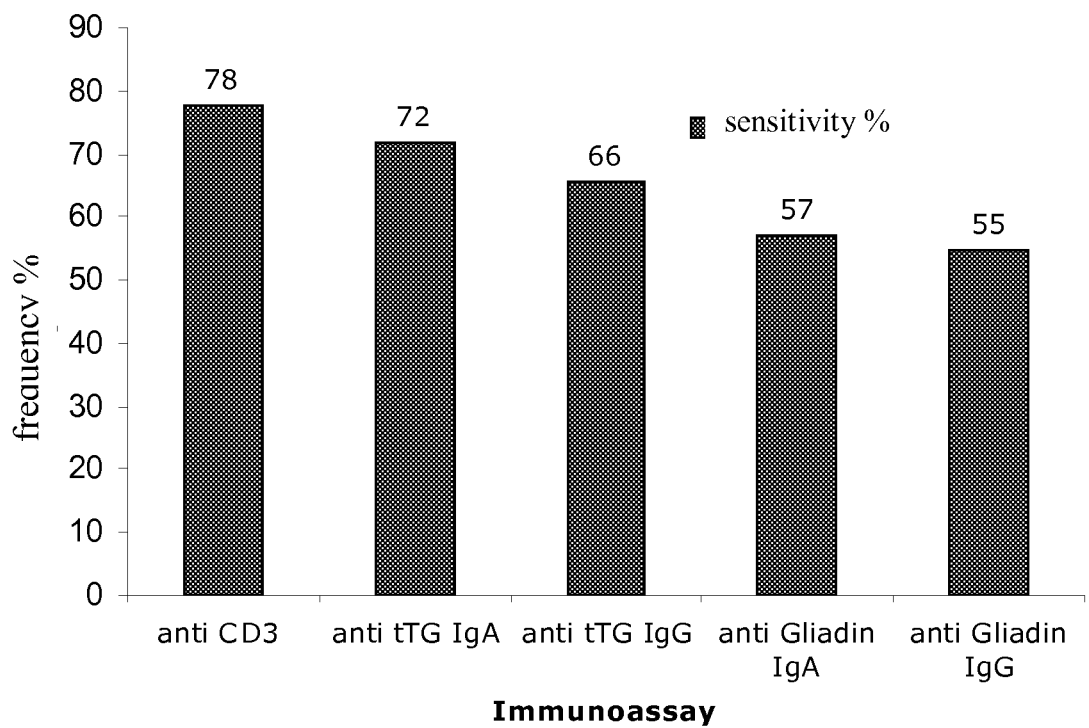
FIG. 1 shows the sensitivities of commercially available anti-gliadin IgA and IgG ELISAs as well as anti-tTG IgA and IgG ELISAs compared to a CD3 ELISA and indicates the % rate of correctly classified celiac patient sera as a measure for the sensitivity of each test.

1. Preparation and Purification of CD3, tTG and CDtTG

CD3 of SEQ ID NO: 4 was prepared by synthesis and biotinylated at the C-terminal lysine residue.

Human tTG2 of SEQ ID NO: 5, hereinafter referred to as tTG, was cloned in a vector with removable 6×His tag (SEQ ID NO: 8) for recombinant expression and expressed according to a standard protocol, isolated using NINTA column purification, and the 6×His (SEQ ID NO: 8) was removed.

CDPtTG of SEQ ID NO: 6, hereinafter referred to as CDtTG, was likewise cloned in a vector with C-terminal 6×His tag (SEQ ID NO: 8) for recombinant expression and expressed according to a standard protocol, isolated using NINTA column purification, and the His tag was removed.

2. ELISA for CD3, tTG (Homemade) and CDtTG

To detect CD3-specific antibodies, a CD3 peptide ELISA was developed wherein biotinylated CD3 of SEQ ID NO: 4 was initially coupled on a neutravidin-coated microtiter plate, followed by the protocol below:

Neutravidin-CD3 Peptide ELISA

The wells of the microtiter plate were initially blocked with PBS/5% MP buffer overnight. Thereafter, the biotinylated peptides were applied using 500 pmol/well in PBS buffer each time. After incubation for 2 h, the CD3/neutravidin-coated plates were washed 4 times with PBS/0.1% TWEEN® and incubated for 1 h with patient serum at a dilution of 1:800 in PBS/2% MP. Thereafter, washing was repeated 4 times, followed by application of peroxidase-conjugated second Ab at a dilution of 1:5000. Incubation was also for 1 hour. Finally, washing was repeated 4 times, followed by application of the substrate. The reaction with development of a blue color was quenched after 5 min using 0.5 M sulfuric acid. The resulting yellow color was measured photometrically at a measurement wavelength of 450 nm versus a reference wavelength of 620 nm using an ELISA reader and visualized with the aid of the Magellan software. Each solution was applied using 100 µl per well. Blocking and the single washing steps were carried out using 300 µl per well each time. The microtiter plates with peptide, patient serum and $2^{nd}$ Ab were incubated with agitation at RT.

CDtTG, tTG ELISA Protocol:

To detect tTG2- or CDPtTG2-specific antibodies, a specific ELISA was developed wherein recombinant tTG of SEQ ID NO: 5 and CDtTG of SEQ ID NO: 6 were initially coupled to a MAXISORB® microtiter plate (Nunc) and the following protocol was subsequently used:

A) Coupling buffer: 100 mM Tris, 10 mM NaCl, pH 7.8
B) Wash buffer: 50 mM Tris-HCl, 150 mM NaCl, 10 mM EDTA, 0.1% Tween 20, pH 7.4
C) Saturation buffer: 50 mM Tris-HCl, 150 mM NaCl, 0.5% BSA, 3% sucrose, pH 7.4
D) Serum dilution buffer: 50 mM Tris-HCl, 150 mM NaCl, 0.5% Tween 20, pH 7.4

Procedure:

Coating on MaxiSorb plates from Nunc: Coating quantity: CDPtTG and tTG were each used at a concentration of 0.5 µg/well.

Coating volume: 100 µl/well. All tTGs were suitably diluted in coupling buffer A. For coating, the plates were incubated at 40° C. overnight.

Blank and $2^{nd}$ Ab controls were carried along in ELISA implementation. The OD values of blank and $2^{nd}$ Ab controls were subtracted in ELISA evaluation.

After coating the plates were washed with 3×300 µl/well wash buffer B. Each wash step corresponds to 600 rpm on the ELISA shaker for 3 min. Thereafter, the plates were blocked with 300 µl/well saturation buffer for 2 h at RT. The sera were diluted 1:800 in serum dilution buffer D and 100 µl/well directly placed on the plates after blocking. Incubation at RT with shaking; washing with 5×300 µl/well wash buffer B.

$2^{nd}$ Ab:
<hIgA>HRP from Dako was diluted 1:1500 in wash buffer B, and 100 µl/well was used;
<hIgG>-HRP from Dako at a dilution of 1:5000 likewise in wash buffer B, and 100 µl/well was used.

Incubation for 1 h at RT with shaking. Washing with 4×300 µl/well wash buffer B. Allowing reaction with 100 µl/well TMB substrate (SERAMUNBLUE® fast) for 5 min. Thereafter, quenching with 100 µl/well quenching soln. (0.5 M $H_2SO_4$) and evaluation in ELISA reader at 450 nm.

3. Cohort of Celiac Patients Sera

In the course of the present work, human patient sera from 91 patients with positive celiac diagnosis, varying age, sex and pathological characteristics were employed. All sera used were obtained from the Department of Clinical Rheumatology at the Charité (Berlin). In addition, 80 sera from normal donors were processed as control group and compared with the group of autoimmune diseases in this work.

4. Comparison of Sensitivities Obtained for CD3 ELISA, tTG ELISA, CDtTG ELISA and Commercially Available Gliadin and tTG ELISAs The sera specified under Section 3 were then used in the ELISA tests specified under Section 2. In parallel, the same sera were also examined with commercially available celiac ELISA tests which react to either gliadin-specific antibodies or antibodies specific to tTG2. To this end, commercial anti-htTG IgA or IgG ELISAs from Generic Assays GmbH (Germany) and commercial anti-gliadin IgA and IgG ELISAs from Generic Assays GmbH (Germany) were used.

As shown in FIG. 1, the CD3-specific ELISA was found to be more sensitive in correct classification of celiac patient sera compared to the commercially available anti-tTG and anti-gliadin ELISAs.

Figure 2:
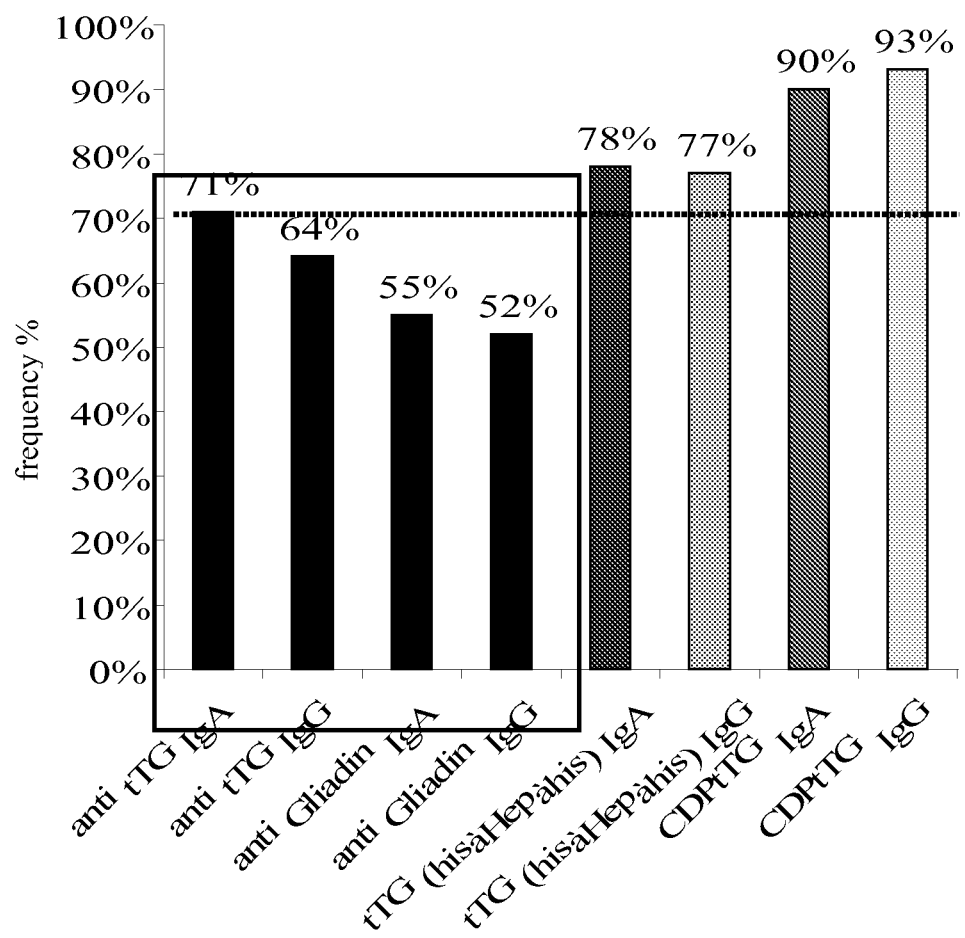
FIG. 2 shows the sensitivities of commercially available anti-gliadin IgA and IgG ELISAs as well as anti-tTG IgA and IgG ELISAs compared to CDPtTG ELISA and tTG ELISA, using the CDPtTG ELISA protocol, and indicates the % rate of correctly classified celiac patient sera as a measure for the sensitivity of each test.

As shown in FIG. 2, ELISAs based on recombinant tTG2 were likewise superior to the commercially available anti-tTG and anti-gliadin ELISAs with respect to sensitivity. The CDPtTG-based ELISA was by far the most sensitive ELISA for correct classification of celiac patient sera. Thus, in total, the presence of the peptide sequence of SEQ ID NO: 1 according to the invention results in a celiac ELISA with improved sensitivity compared to commercial ELISAs and an anti-tTG ELISA carried out under the same conditions as the CDPtTG ELISA.

Thus, it was shown that peptides comprising the peptide sequence of SEQ ID NO: 1 according to the invention are informative and can be used in the diagnosis of celiac disease. Also, it was shown that an ELISA based on a peptide comprising the peptide according to the invention of SEQ ID NO: 1 has improved sensitivity.

FIG. 3 illustrates overlaps in the sensitivities of the CD3 ELISA with the commercially available anti-gliadin and anti-tTG ELISAs. It was found that the CD3 ELISA can detect sera from celiac patients that were not recognized by one or more or even all of the commercially available ELISA tests used. Thus, the use of a celiac assay based on a peptide comprising the peptide sequence of SEQ ID NO: 1 provides a valuable contribution to complete serological detection and diagnosis of celiac disease patients.

5. CD3-specific Antibodies from Patient Sera

Affinity Purification of CD3 Antibodies

For isolation and purification of the affinity-specific antibodies against the CD3 peptide from patient sera, the biotinylated variant of the CD3 peptide was coupled to avidin or neutravidin microtiter plates, followed by using a pool of 24 strongly positive celiac sera with minor nonspecific background binding for immune complex formation. Initially, the microtiter plate (MTP) was blocked with PBST/5% MP for 1 h at RT. This was followed by 3 washings with PBS wash buffer, and the wells of the 96-well plate was coated with 5000 pmol/well CD3 peptide, which corresponds to a 10-fold capacity per well. After incubation at RT for 1 hour, the plate was washed 3 times with wash buffer. Thereafter, the sera were applied to the streptavidin plate or NEUTRAVIDIN® plate, to which end each patient serum was initially diluted 1:100 in PBST/2% MP. Subsequently, the sera were pooled and placed in the wells using a volume of 100 µl/well. This was followed by incubation for 1 hour at RT. Thereafter, the contents of all wells were removed and recombined and used in another purification cycle or as a control for the affinity-specific purification effect in another purification cycle with the negative control peptide, Bor21 in the present case. After removal of the sera the plate was washed 4 times with wash buffer. The wells were subsequently spiked with 150 µl/well glycine elution buffer and incubated on the shaker for 10 min.

Finally, the elution buffer was resuspended several times and removed from the wells and immediately combined with 1:10 1 M Tris-HCl pH 8.0 buffer. This was immediately followed by rebuffering by ultracentrifugation in AMICON® FALCONS® with a membrane cutoff of 55 kDa, using 5× a 5-fold volume of PBS buffer as counterbuffer. As control of success the batch was tested in the CD3 ELISA with positive and negative control sera. The quantities of antibodies thus obtained were stored at 4° C. in PBS and used in further immunological tests.

All wash steps were performed using a volume of 300 μl/well. Furthermore, all incubation steps were carried out at RT on the ELISA plate shaker at a rotational speed of 600 rpm.

Figure 4:
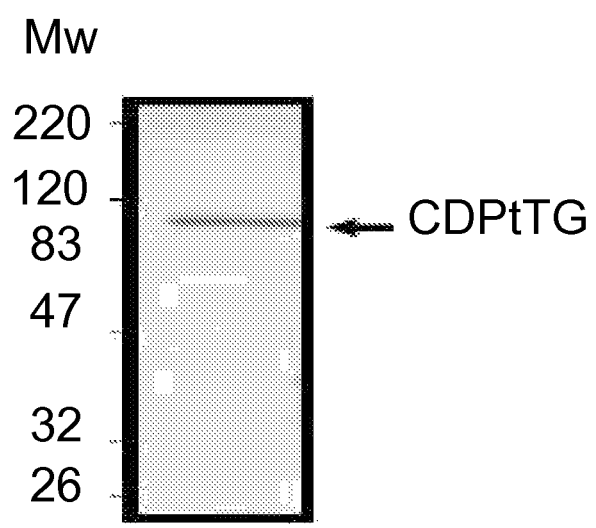
FIG. 4 shows that CD3-specific antibodies isolated from patient sera can specifically recognize CDPtTG in a Western blot.

As shown in FIG. 4, the CD3 peptide antibodies thus isolated react specifically with CDPtTG in a Western blot experiment. From this it follows that the antigen in the CD3 peptide is not a conformational antigen, but can also be detected in denatured state by CD3 peptide antibodies isolated from patient sera. Consequently, peptides comprising the peptide according to the invention of SEQ ID NO: 1 are not only suitable for use in diagnostic tests focusing on antigens in native state, but also for test formats wherein the antigen is used in denatured state, such as Western blot assays, protein arrays, LUMINEX® bead arrays and/or protein chip assays.

---

The invention claimed is:

1. A peptide comprising the amino acid sequence of SEQ ID NO: 1.

2. The peptide of claim 1, characterized in that the peptide comprises an amino acid sequence selected from the group consisting of SEQ ID NO: 2, SEQ ID NO: 3, and SEQ ID NO: 4.

3. The peptide of claim 1, characterized in that the peptide comprises additional amino acids, one or more linkers and/or one or more functional groups.

4. The peptide of claim 1, characterized in that the peptide additionally comprises a sequence of at least 25 consecutive amino acids from SEQ ID NO: 5.

5. The peptide of claim 1, characterized in that the peptide comprises an amino acid sequence selected from the group consisting of SEQ ID NO: 6 and SEQ ID NO: 7.

6. A method for the in vitro detection of antibodies against the peptide of claim 1 in a sample, comprising the steps of:
   i) contacting a sample with the peptide of claim 1 in vitro, and
   ii) detecting binding of antibodies in the sample to the peptide, thereby detecting the antibodies.

7. The method of claim 6, characterized in that the sample is a body fluid or is obtained from a body fluid.

8. The method of claim 6, characterized in that the peptide is immobilized on a support.

9. The method of claim 6, characterized in that the method is carried out in an ELISA format.

10. A kit for performing the method of claim 6, said kit comprising the peptide of claim 1 immobilized on a support.

11. The kit of claim 10, characterized in that the kit is an ELISA or strip test.

12. A nucleic acid comprising a nucleic acid sequence encoding SEQ ID NO:1.

13. A transformed microorganism transformed with a vector comprising the nucleic acid of claim 12, or a transfected cell transfected with a vector comprising the nucleic acid of claim 12.

* * * * *

SEQUENCE LISTING

```
<160> NUMBER OF SEQ ID NOS: 8

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Phe Pro Gln Pro Glu Gln Pro Phe Gln Pro Glu Gln Pro Phe Gln
1               5                   10                  15

Glu Gln Pro Phe Pro Gln Pro Glu
            20

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Glu Gln Pro Phe Pro Gln Pro Glu Gln Pro Phe Gln Pro Glu Gln
1               5                   10                  15

Pro Phe Gln Glu Gln Pro Phe Pro Gln Pro Glu Gln Pro Phe
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Glu Gln Pro Phe Pro Gln Pro Glu Gln Pro Phe Gln Pro Glu Gln
1               5                   10                  15

Pro Phe Gln Glu Gln Pro Phe Pro Gln Pro Glu Gln Pro Phe Lys
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Lys is biotinylated

<400> SEQUENCE: 4
```

-continued

```
Gln Glu Gln Pro Phe Pro Gln Pro Glu Gln Pro Phe Gln Pro Glu Gln
1               5                   10                  15

Pro Phe Gln Glu Gln Pro Phe Pro Gln Pro Glu Gln Pro Phe Lys
                20                  25                  30
```

<210> SEQ ID NO 5
<211> LENGTH: 687
<212> TYPE: PRT
<213> ORGANISM: Homo sapiens

<400> SEQUENCE: 5

```
Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
                20                  25                  30

Val Arg Arg Gly Gln Pro Phe Trp Leu Thr Leu His Phe Glu Gly Arg
            35                  40                  45

Asn Tyr Glu Ala Ser Val Asp Ser Leu Thr Phe Ser Val Val Thr Gly
        50                  55                  60

Pro Ala Pro Ser Gln Glu Ala Gly Thr Lys Ala Arg Phe Pro Leu Arg
65                  70                  75                  80

Asp Ala Val Glu Glu Gly Asp Trp Thr Ala Thr Val Val Asp Gln Gln
                85                  90                  95

Asp Cys Thr Leu Ser Leu Gln Leu Thr Thr Pro Ala Asn Ala Pro Ile
                100                 105                 110

Gly Leu Tyr Arg Leu Ser Leu Glu Ala Ser Thr Gly Tyr Gln Gly Ser
            115                 120                 125

Ser Phe Val Leu Gly His Phe Ile Leu Leu Phe Asn Ala Trp Cys Pro
130                 135                 140

Ala Asp Ala Val Tyr Leu Asp Ser Glu Glu Glu Arg Gln Glu Tyr Val
145                 150                 155                 160

Leu Thr Gln Gln Gly Phe Ile Tyr Gln Gly Ser Ala Lys Phe Ile Lys
                165                 170                 175

Asn Ile Pro Trp Asn Phe Gly Gln Phe Glu Asp Gly Ile Leu Asp Ile
                180                 185                 190

Cys Leu Ile Leu Leu Asp Val Asn Pro Lys Phe Leu Lys Asn Ala Gly
            195                 200                 205

Arg Asp Cys Ser Arg Arg Ser Ser Pro Val Tyr Val Gly Arg Val Val
210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Val Ser Pro Met Ser Trp Ile Gly
                245                 250                 255

Ser Val Asp Ile Leu Arg Arg Trp Lys Asn His Gly Cys Gln Arg Val
                260                 265                 270

Lys Tyr Gly Gln Cys Trp Val Phe Ala Ala Val Ala Cys Thr Val Leu
            275                 280                 285

Arg Cys Leu Gly Ile Pro Thr Arg Val Val Thr Asn Tyr Asn Ser Ala
290                 295                 300

His Asp Gln Asn Ser Asn Leu Leu Ile Glu Tyr Phe Arg Asn Glu Phe
305                 310                 315                 320

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
```

```
            340                 345                 350
Gly Trp Gln Ala Leu Asp Pro Thr Pro Gln Glu Lys Ser Glu Gly Thr
            355                 360                 365

Tyr Cys Cys Gly Pro Val Pro Val Arg Ala Ile Lys Glu Gly Asp Leu
370                 375                 380

Ser Thr Lys Tyr Asp Ala Pro Phe Val Phe Ala Glu Val Asn Ala Asp
385                 390                 395                 400

Val Val Asp Trp Ile Gln Gln Asp Gly Ser Val His Lys Ser Ile
                405                 410                 415

Asn Arg Ser Leu Ile Val Gly Leu Lys Ile Ser Thr Lys Ser Val Gly
                420                 425                 430

Arg Asp Glu Arg Glu Asp Ile Thr His Thr Tyr Lys Tyr Pro Glu Gly
                435                 440                 445

Ser Ser Glu Glu Arg Glu Ala Phe Thr Arg Ala Asn His Leu Asn Lys
                450                 455                 460

Leu Ala Glu Lys Glu Glu Thr Gly Met Ala Met Arg Ile Arg Val Gly
465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Cys Ala Arg
                500                 505                 510

Thr Val Ser Tyr Asn Gly Ile Leu Gly Pro Glu Cys Gly Thr Lys Tyr
                515                 520                 525

Leu Leu Asn Leu Asn Leu Glu Pro Phe Ser Gly Lys Ser Val Pro Leu
                530                 535                 540

Cys Ile Leu Tyr Glu Lys Tyr Arg Asp Cys Leu Thr Glu Ser Asn Leu
545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
                580                 585                 590

Ile Leu Gly Glu Pro Lys Gln Lys Arg Lys Leu Val Ala Glu Val Ser
                595                 600                 605

Leu Gln Asn Pro Leu Pro Val Ala Leu Glu Gly Cys Thr Phe Thr Val
                610                 615                 620

Glu Gly Ala Gly Leu Thr Glu Glu Gln Lys Thr Val Glu Ile Pro Asp
625                 630                 635                 640

Pro Val Glu Ala Gly Glu Glu Val Lys Val Arg Met Asp Leu Leu Pro
                645                 650                 655

Leu His Met Gly Leu His Lys Leu Val Val Asn Phe Glu Ser Asp Lys
                660                 665                 670

Leu Lys Ala Val Lys Gly Phe Arg Asn Val Ile Ile Gly Pro Ala
                675                 680                 685

<210> SEQ ID NO 6
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Glu Glu Leu Val Leu Glu Arg Cys Asp Leu Glu Leu Glu Thr
1               5                   10                  15
```

```
Asn Gly Arg Asp His His Thr Ala Asp Leu Cys Arg Glu Lys Leu Val
            20                  25                  30
Val Arg Arg Gly Gln Pro Phe Trp Leu Thr Leu His Phe Glu Gly Arg
        35                  40                  45
Asn Tyr Glu Ala Ser Val Asp Ser Leu Thr Phe Ser Val Val Thr Gly
    50                  55                  60
Pro Ala Pro Ser Gln Glu Ala Gly Thr Lys Ala Arg Phe Pro Leu Arg
65                  70                  75                  80
Asp Ala Val Glu Glu Gly Asp Trp Thr Ala Thr Val Val Asp Gln Gln
                85                  90                  95
Asp Cys Thr Leu Ser Leu Gln Leu Thr Thr Pro Ala Asn Ala Pro Ile
            100                 105                 110
Gly Leu Tyr Arg Leu Ser Leu Glu Ala Ser Thr Gly Tyr Gln Gly Ser
        115                 120                 125
Ser Phe Val Leu Gly His Phe Ile Leu Leu Phe Asn Ala Trp Cys Pro
    130                 135                 140
Ala Asp Ala Val Tyr Leu Asp Ser Glu Glu Arg Gln Glu Tyr Val
145                 150                 155                 160
Leu Thr Gln Gln Gly Phe Ile Tyr Gln Gly Ser Ala Lys Phe Ile Lys
                165                 170                 175
Asn Ile Pro Trp Asn Phe Gly Gln Phe Glu Asp Gly Ile Leu Asp Ile
            180                 185                 190
Cys Leu Ile Leu Leu Asp Val Asn Pro Lys Phe Leu Lys Asn Ala Gly
        195                 200                 205
Arg Asp Cys Ser Arg Arg Ser Ser Pro Val Tyr Val Gly Arg Val Val
    210                 215                 220
Ser Gly Met Val Asn Cys Asn Asp Asp Gln Gly Val Leu Leu Gly Arg
225                 230                 235                 240
Trp Asp Asn Asn Tyr Gly Asp Gly Val Ser Pro Met Ser Trp Ile Gly
                245                 250                 255
Ser Val Asp Ile Leu Arg Arg Trp Lys Asn His Gly Cys Gln Arg Val
            260                 265                 270
Lys Tyr Gly Gln Cys Trp Val Phe Ala Ala Val Ala Cys Thr Val Leu
        275                 280                 285
Arg Cys Leu Gly Ile Pro Thr Arg Val Val Thr Asn Tyr Asn Ser Ala
    290                 295                 300
His Asp Gln Asn Ser Asn Leu Leu Ile Glu Tyr Phe Arg Asn Glu Phe
305                 310                 315                 320
Gly Glu Ile Gln Gly Asp Lys Ser Glu Met Ile Trp Asn Phe His Cys
                325                 330                 335
Trp Val Glu Ser Trp Met Thr Arg Pro Asp Leu Gln Pro Gly Tyr Glu
            340                 345                 350
Gly Trp Gln Ala Leu Asp Pro Thr Pro Gln Glu Lys Ser Glu Gly Thr
        355                 360                 365
Tyr Cys Cys Gly Pro Val Pro Val Arg Ala Ile Lys Glu Gly Asp Leu
    370                 375                 380
Ser Thr Lys Tyr Asp Ala Pro Phe Val Phe Ala Glu Val Asn Ala Asp
385                 390                 395                 400
Val Val Asp Trp Ile Gln Gln Asp Gly Ser Val His Lys Ser Ile
                405                 410                 415
Asn Arg Ser Leu Ile Val Gly Leu Lys Ile Ser Thr Lys Ser Val Gly
            420                 425                 430
Arg Asp Glu Arg Glu Asp Ile Thr His Thr Tyr Lys Tyr Pro Glu Gly
```

```
              435                 440                 445
Ser Ser Glu Glu Arg Glu Ala Phe Thr Arg Ala Asn His Leu Asn Lys
    450                 455                 460

Leu Ala Glu Lys Glu Glu Thr Gly Met Ala Met Arg Ile Arg Val Gly
465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Cys Ala Arg
                500                 505                 510

Thr Val Ser Tyr Asn Gly Ile Leu Gly Pro Glu Cys Gly Thr Lys Tyr
            515                 520                 525

Leu Leu Asn Leu Asn Leu Glu Pro Phe Ser Glu Lys Ser Val Pro Leu
        530                 535                 540

Cys Ile Leu Tyr Glu Lys Tyr Arg Asp Cys Leu Thr Glu Ser Asn Leu
545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
            580                 585                 590

Ile Leu Gly Glu Pro Lys Gln Lys Arg Lys Leu Val Ala Glu Val Ser
        595                 600                 605

Leu Gln Asn Pro Leu Pro Val Ala Leu Glu Gly Cys Thr Phe Thr Val
    610                 615                 620

Glu Gly Ala Gly Leu Thr Glu Glu Gln Lys Thr Val Glu Ile Pro Asp
625                 630                 635                 640

Pro Val Glu Ala Gly Glu Val Lys Val Arg Met Asp Leu Leu Pro
                645                 650                 655

Leu His Met Gly Leu His Lys Leu Val Val Asn Phe Glu Ser Asp Lys
            660                 665                 670

Leu Lys Ala Val Lys Gly Phe Arg Asn Val Ile Ile Gly Pro Ala Gln
        675                 680                 685

Glu Gln Pro Phe Pro Gln Pro Glu Gln Pro Phe Gln Pro Glu Gln Pro
    690                 695                 700

Phe Gln Glu Gln Pro Phe Pro Gln Pro Glu Gln Pro Phe
705                 710                 715

<210> SEQ ID NO 7
<211> LENGTH: 747
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
            20                  25                  30

Val Arg Arg Gly Gln Pro Phe Trp Leu Thr Leu His Phe Glu Gly Arg
        35                  40                  45

Asn Tyr Glu Ala Ser Val Asp Ser Leu Thr Phe Ser Val Val Thr Gly
    50                  55                  60

Pro Ala Pro Ser Gln Glu Ala Gly Thr Lys Ala Arg Phe Pro Leu Arg
65                  70                  75                  80
```

```
Asp Ala Val Glu Glu Gly Asp Trp Thr Ala Thr Val Asp Gln Gln
                85                  90                  95
Asp Cys Thr Leu Ser Leu Gln Leu Thr Thr Pro Ala Asn Ala Pro Ile
            100                 105                 110
Gly Leu Tyr Arg Leu Ser Leu Glu Ala Ser Thr Gly Tyr Gln Gly Ser
            115                 120                 125
Ser Phe Val Leu Gly His Phe Ile Leu Leu Phe Asn Ala Trp Cys Pro
            130                 135                 140
Ala Asp Ala Val Tyr Leu Asp Ser Glu Glu Arg Gln Glu Tyr Val
145                 150                 155                 160
Leu Thr Gln Gln Gly Phe Ile Tyr Gln Gly Ser Ala Lys Phe Ile Lys
            165                 170                 175
Asn Ile Pro Trp Asn Phe Gly Gln Phe Glu Asp Gly Ile Leu Asp Ile
            180                 185                 190
Cys Leu Ile Leu Leu Asp Val Asn Pro Lys Phe Leu Lys Asn Ala Gly
            195                 200                 205
Arg Asp Cys Ser Arg Arg Ser Pro Val Tyr Val Gly Arg Val Val
    210                 215                 220
Ser Gly Met Val Asn Cys Asn Asp Asp Gln Gly Val Leu Leu Gly Arg
225                 230                 235                 240
Trp Asp Asn Asn Tyr Gly Asp Gly Val Ser Pro Met Ser Trp Ile Gly
            245                 250                 255
Ser Val Asp Ile Leu Arg Arg Trp Lys Asn His Gly Cys Gln Arg Val
            260                 265                 270
Lys Tyr Gly Gln Cys Trp Val Phe Ala Ala Val Ala Cys Thr Val Leu
            275                 280                 285
Arg Cys Leu Gly Ile Pro Thr Arg Val Val Thr Asn Tyr Asn Ser Ala
            290                 295                 300
His Asp Gln Asn Ser Asn Leu Leu Ile Glu Tyr Phe Arg Asn Glu Phe
305                 310                 315                 320
Gly Glu Ile Gln Gly Asp Lys Ser Glu Met Ile Trp Asn Phe His Cys
            325                 330                 335
Trp Val Glu Ser Trp Met Thr Arg Pro Asp Leu Gln Pro Gly Tyr Glu
            340                 345                 350
Gly Trp Gln Ala Leu Asp Pro Thr Pro Gln Glu Lys Ser Glu Gly Thr
            355                 360                 365
Tyr Cys Cys Gly Pro Val Pro Val Arg Ala Ile Lys Glu Gly Asp Leu
    370                 375                 380
Ser Thr Lys Tyr Asp Ala Pro Phe Val Phe Ala Glu Val Asn Ala Asp
385                 390                 395                 400
Val Val Asp Trp Ile Gln Gln Asp Asp Gly Ser Val His Lys Ser Ile
            405                 410                 415
Asn Arg Ser Leu Ile Val Gly Leu Lys Ile Ser Thr Lys Ser Val Gly
            420                 425                 430
Arg Asp Glu Arg Glu Asp Ile Thr His Thr Tyr Lys Tyr Pro Glu Gly
    435                 440                 445
Ser Ser Glu Glu Arg Glu Ala Phe Thr Arg Ala Asn His Leu Asn Lys
    450                 455                 460
Leu Ala Glu Lys Glu Glu Thr Gly Met Ala Met Arg Ile Arg Val Gly
465                 470                 475                 480
Gln Ser Met Asn Met Gly Ser Asp Phe Asp Val Phe Ala His Ile Thr
            485                 490                 495
Asn Asn Thr Ala Glu Glu Tyr Val Cys Arg Leu Leu Leu Cys Ala Arg
```

```
                    500                 505                 510
Thr Val Ser Tyr Asn Gly Ile Leu Gly Pro Glu Cys Gly Thr Lys Tyr
            515                 520                 525

Leu Leu Asn Leu Asn Leu Glu Pro Phe Ser Glu Lys Ser Val Pro Leu
            530                 535                 540

Cys Ile Leu Tyr Glu Lys Tyr Arg Asp Cys Leu Thr Glu Ser Asn Leu
545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
            580                 585                 590

Ile Leu Gly Glu Pro Lys Gln Lys Arg Lys Leu Val Ala Glu Val Ser
            595                 600                 605

Leu Gln Asn Pro Leu Pro Val Ala Leu Glu Gly Cys Thr Phe Thr Val
            610                 615                 620

Glu Gly Ala Gly Leu Thr Glu Glu Gln Lys Thr Val Glu Ile Pro Asp
625                 630                 635                 640

Pro Val Glu Ala Gly Glu Val Lys Val Arg Met Asp Leu Leu Pro
                645                 650                 655

Leu His Met Gly Leu His Lys Leu Val Val Asn Phe Glu Ser Asp Lys
            660                 665                 670

Leu Lys Ala Val Lys Gly Phe Arg Asn Val Ile Ile Gly Pro Ala Gln
            675                 680                 685

Glu Gln Pro Phe Pro Gln Pro Glu Gln Pro Phe Gln Pro Glu Gln Pro
            690                 695                 700

Phe Gln Glu Gln Pro Phe Pro Gln Pro Glu Gln Pro Phe Gln Glu Gln
705                 710                 715                 720

Pro Phe Pro Gln Pro Glu Gln Pro Phe Gln Pro Glu Gln Pro Phe Gln
                725                 730                 735

Glu Gln Pro Phe Pro Gln Pro Glu Gln Pro Phe
            740                 745

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5
```